(12) United States Patent
Khaldi et al.

(10) Patent No.: US 12,398,180 B2
(45) Date of Patent: Aug. 26, 2025

(54) TREATMENT OF NON-ALCOHOLIC FATTY LIVER DISEASE

(71) Applicant: NURITAS LIMITED, Dublin (IE)

(72) Inventors: Nora Khaldi, Dublin (IE); Alessandro Adelfio, Dublin (IE); Cyril Lopez, Dublin (IE)

(73) Assignee: NURITAS LIMITED, Dublin (IE)

( * ) Notice: Subject to any disclaimer, the term of this patent is extended or adjusted under 35 U.S.C. 154(b) by 0 days.

(21) Appl. No.: 17/768,356

(22) PCT Filed: Oct. 22, 2020

(86) PCT No.: PCT/EP2020/079836
§ 371 (c)(1),
(2) Date: Apr. 12, 2022

(87) PCT Pub. No.: WO2021/078912
PCT Pub. Date: Apr. 29, 2021

(65) Prior Publication Data
US 2024/0150403 A1    May 9, 2024

(30) Foreign Application Priority Data
Oct. 22, 2019   (EP) .................... 19204536

(51) Int. Cl.
*A61P 1/16*  (2006.01)
*A61K 38/00* (2006.01)
*A61K 38/08* (2019.01)
*C07K 7/52*  (2006.01)

(52) U.S. Cl.
CPC ............... *C07K 7/52* (2013.01); *A61K 38/08* (2013.01); *A61P 1/16* (2018.01); *A61K 38/00* (2013.01)

(58) Field of Classification Search
None
See application file for complete search history.

(56) References Cited

U.S. PATENT DOCUMENTS 10,729,636 B2 *   8/2020   Khaldi ................. A61K 38/07

FOREIGN PATENT DOCUMENTS

WO   2018104346 A1   6/2018

OTHER PUBLICATIONS

Gharaibeh et al. "SGLT-2 inhibitors as promising therapeutics for non-alcoholic fatty liver disease: pathophysiology, clinical outcomes, and future directions." Diabetes, Metabolic Syndrome and Obesity: Targets and Therapy 12 (2019): 1001.
Guss et al. "Liraglutide's use in treatment of non-alcoholic fatty liver: an evaluation of the non-alcoholic steatohepatitis study." Hepatobiliary surgery and nutrition 5.6 (2016): 515.
Romero-Gomez et al. "Treatment of NAFLD with diet, physical activity and exercise." Journal of hepatology 67.4 (2017): 829-846.

* cited by examiner

*Primary Examiner* — Christina Bradley
(74) *Attorney, Agent, or Firm* — NIXON PEABODY LLP; David S. Resnick; Nicole D. Kling

(57) ABSTRACT

The Applicant has discovered that the peptide of SEQUENCE ID NO: 1 (WKDEAGKPLVK) mediates changes in key biomarker activities associated with NASH (Table 1), and that the peptide is capable of penetrating HepG2 liver cells in a hepatic cell penetration assay (FIG. 1). In addition, the Applicant demonstrates that treatment with pep_260 (SEQ ID 1) for 44 days significantly relieves macro-vesicular steatosis in obese diabetic KKAy mice (FIG. 2) In a first aspect, the invention relates to the use of a peptide comprising SEQUENCE ID NO: 1, or a functional (or therapeutically effective) variant or functional fragment of SEQUENCE ID NO: 1 (hereafter "peptide active agent" or "peptide of the invention"), in a method for the treatment or prevention of non-alcoholic fatty liver disease (NAFLD), in particular non-alcoholic steatohepatitis (NASH), in a mammal.

10 Claims, 6 Drawing Sheets
Specification includes a Sequence Listing.

A

B

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 1

Trp Lys Asp Glu Ala Gly Lys Pro Leu Val Lys
1               5                   10

<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Lys
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (10)..(10)
<223> OTHER INFORMATION: D-Val
<220> FEATURE:
<221> NAME/KEY: MOD_RES
<222> LOCATION: (11)..(11)
<223> OTHER INFORMATION: D-Lys

<400> SEQUENCE: 2

Xaa Xaa Asp Glu Xaa Gly Lys Pro Leu Xaa Xaa
1               5                   10

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(5)
<223> OTHER INFORMATION: /note="This sequence contains a thioether
      cyclization between the n-terminus and the Cys residue at position
      5"
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (4)..(4)
<223> OTHER INFORMATION: Glu(Me)
<220> FEATURE:
<221> NAME/KEY: MOD_RES
<222> LOCATION: (8)..(8)
<223> OTHER INFORMATION: Pro(Me)
<220> FEATURE:
<221> NAME/KEY: MOD_RES
<222> LOCATION: (11)..(11)
<223> OTHER INFORMATION: D-Lys
<220> FEATURE:
```

```
<221> NAME/KEY: source
<223> OTHER INFORMATION: /note="C-term OH"

<400> SEQUENCE: 3

Xaa Lys Glu Xaa Cys Gly Lys Xaa Leu Val Xaa
1               5                   10
```

TREATMENT OF NON-ALCOHOLIC FATTY LIVER DISEASE

CROSS-REFERENCE TO RELATED APPLICATIONS

This application is a 35 U.S.C. § 371 National Phase Entry Application of International Application No. PCT/EP2020/079836 filed Oct. 22, 2020, which designates the U.S. and claims benefit under 35 U.S.C. § 119(a) of EP Provisional Application No. 19204536.7 filed Oct. 22, 2019, the contents of which are incorporated herein by reference in their entireties.

FIELD OF THE INVENTION

The present invention relates to treatment of non-alcoholic fatty liver disease (NAFLD), in particular non-alcoholic steatohepatitis (NASH), in a mammal.

BACKGROUND TO THE INVENTION

NASH is a widespread, severe, and "silent" liver disease that can lead to cirrhosis or cancer, and which affects millions of people around the world—including children. In a biopsy-proven study, it was shown that 12% of US adults have NASH, with a 63% increase expected by 2030; NAFLD rates are alarming with 31% in South America, 32% in Middle-East, 23% in Europe, and a worrying 10% in children already. With prevalence rising and closely associated with modern lifestyles linked to the pre-diabetes, type 2 diabetes and obesity epidemics—NASH is expected to become the leading cause for liver transplantation in the United States by 2020;

NASH is a looming public health threat, not only because of the high cost of a liver transplant (~$800 k per patient in the United States) and associated complications, but also because NASH is closely associated with non-hepatic disorders such as cardiovascular events which are the leading cause of death in NASH patients. NASH remains predominantly unknown in the public because it is a silent disease, displaying no symptoms, meaning that most patients with NASH are not diagnosed. NASH is also under-diagnosed because it is difficult to detect due to the lack of a simple, accurate and cost-effective diagnostic solution. NASH patients must fight through stigmas and misconceptions associated with the disease. They also lack access to easy-to-digest information to help them explain their condition to relatives, friend and colleagues who often have trouble understanding its nature and consequences;

Apart from a few international experts, the medical community—including diabetologists, endocrinologists, obesity specialists, cardiologists, obstetrician-gynecologists, general practitioners and nurses—remains largely under-informed, with limited opportunities to learn about the disease and limited relevant educational resources;

While there is still no approved treatment available today, several advanced development programs are underway, providing hope to millions of clinicians and patients worldwide (only 10% of patients are able to successfully fight the disease through challenging lifestyle changes).

It is an object of the invention to overcome at least one of the above-referenced problems.

SUMMARY OF THE INVENTION

The Applicant has discovered that the peptide of SEQUENCE ID NO: 1 (WKDEAGKPLVK) mediates changes in key biomarker activities associated with NASH (Table 1), and that the peptide is capable of penetrating HepG2 liver cells in a hepatic cell penetration assay (FIG. 1). In addition, the Applicant demonstrates that treatment with SEQ ID 1 for 44 days significantly relieves macrovesicular steatosis in obese diabetic KKAy mice (FIG. 2).

The Applicant also provides a variant of SEQ ID 1, {d}W{d}KDE{d}AGKPL{d}V{d}K (SEQUENCE ID NO: 2), having five modified residues (residues 1, 2, 5, 10, 11 are provided as D-amino acids) compared with SEQ ID 1. The variant peptide of SEQ ID 2 significantly enhances glucose uptake into skeletal muscle cells compared with insulin (FIG. 3), significantly reduces HbA1c % (amount of glucose attached to body's red blood cells) compared with Liraglutide (FIG. 4), and exhibits an optimised PK profile of $T^{1/2}$=93 minutes.

Also provided is a cyclised variant of SEQ ID 1-(1(clac)wKE(Me)EC1GK(Me)PLVk-OH) (SEQUENCE ID NO: 3) that exhibits enhanced stability in-vivo and significantly increases glucose uptake in human skeletal muscle cells in-vitro (FIG. 5).

Bioactive peptides carry advantageous safety profiles and the ability to engage targets that can attenuate numerous pathways.

In a first aspect, the invention relates to the use of a peptide comprising SEQUENCE ID NO: 1, or a functional (or therapeutically effective) variant or functional fragment of SEQUENCE ID NO: 1 (hereafter "peptide active agent" or "peptide of the invention"), in a method for the treatment or prevention of non-alcoholic fatty liver disease (NAFLD), in particular non-alcoholic steatohepatitis (NASH), in a mammal.

In another aspect, the invention relates to a method for the treatment or prevention of non-alcoholic fatty liver disease (NAFLD), non-alcoholic steatohepatitis (NASH), in a mammal, comprising a step of administering to the mammal a therapeutically effective amount of a peptide comprising SEQUENCE ID NO: 1, or a functional (or therapeutically effective) variant or functional fragment of SEQUENCE ID NO: 1 (hereafter "peptide active agent")

The peptide (or functional variant or fragment) may be administered alone or in combination with other co-drugs that provide an enhanced therapeutic effect, which include but not limited to, drugs which have identified effect in the treatment of diabetes or obesity, In one embodiment, the peptide has up to 40, 35, 30, 25, 20, or 15 amino acids. In one embodiment, the peptide has 11-15 amino acids. In one embodiment, the peptide consists essentially of SEQUENCE ID NO: 1.

In one embodiment, the variant of the peptide has 1-6 modifications compared with SEQUENCE ID NO: 1, each modification typically independently selected from insertion addition, deletion, and substitution (ideally conservative substitution). In one embodiment, one or more amino acids (for example 1-5, 1-4, −1-3, or 1-2) are replaced with D-amino acids.

In one embodiment, one or more of residues 1, 2, 5, 10, 11 are replaced with D-amino acids, for example 2, 3, 4, or 5 of the residues. In one embodiment, one or more amino acids are replaced with conservative amino acid substitutions. In one embodiment, the functional variant has a sequence {d}W{d}KDE{d}AGKPL{d}V{d}K (SEQUENCE ID NO: 2), which is the 50 same as SEQ ID 1 with the exception that amino acids 1, 2, 5, 10 and 11 are replaced with D-form of the amino acid.

In one embodiment, the peptide is modified. In one embodiment, the peptide is a recombinant peptide. In one embodiment, the peptide is cyclised. An example of a cyclised peptide is (1(clac)wKE(Me)EC1GK(Me)PLVk-OH)—SEQ ID 3. In this variant, the residues "w" and ""k" are D-amino acids, the residues "E" and "P" are methylated, and the peptide comprises a thioether cyclization between the n-terminus and the cysteine residue, in which "1(clac)" and "C1" indicate the two ends of the cycle.

In another embodiment, the peptide may be administered alone or in combination with other co-drugs that provide an enhanced therapeutic effect, which include but not limited to, drugs which have identified effect in the treatment of diabetes or obesity, In another aspect, the invention provides a peptide having a sequence {d}W{d}KDE{d}AGKPL{d}V{d}K (SEQ ID 2). In another embodiment, the invention provides a cyclised peptide of (1(clac)wKE(Me)EC1GK(Me)PLVk-OH)—SEQ ID 3.

The peptide of the invention may be a composition or pharmaceutical composition comprising the peptide of the invention.

In another aspect, the invention provides a nucleic acid encoding a peptide of the invention.

In another aspect, the invention provides an expression vector comprising DNA encoding a peptide of the invention, in which the vector is configured for heterologous expression of the peptide of the invention, in a host cell (hereafter "expression vector of the invention").

In another aspect, the invention provides a host cell, especially a bacterium or mammalian producer cell, engineered to heterologously express a peptide of the invention (hereafter "transformed cell of the invention"). In one embodiment, the transformed host cell comprises an expression vector on the invention.

Other aspects and preferred embodiments of the invention are defined and described in the other claims set out below.

DETAILED DESCRIPTION OF THE INVENTION

Figure 1:
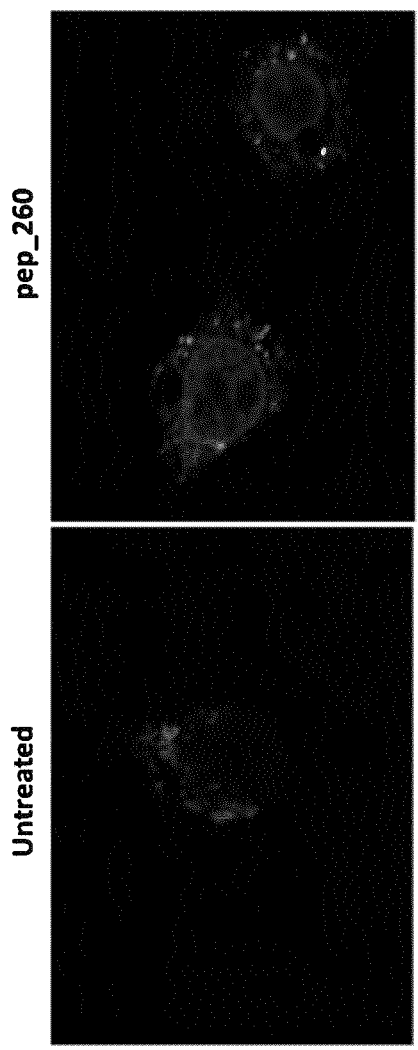
FIG. 1: Cell Penetration in Liver Cells. HepG2 liver cells treated with Cy5 labelled pep_260 (SEQ ID 1) or Cy5 only (untreated) for 60 min.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. 50 features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the subject's physical size, age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure. Improvement may be observed in biological/molecular markers, clinical or observational improvements. In a preferred embodiment, the methods of the invention are applicable to humans, large racing animals (horses, camels, dogs), and domestic companion animals (cats and dogs).

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, asses, kiang and zebra.

"Pharmaceutical compositions": A further aspect of the invention relates to a pharmaceutical composition comprising a peptide active agent, admixed with one or more pharmaceutically acceptable diluents, excipients or carriers, or co-administered with other drugs which enhance the therapeutic effect. Even though the peptide active agent can be administered alone, they will generally be administered in admixture with a pharmaceutical carrier, excipient or diluent, particularly for human therapy. The pharmaceutical compositions may be for human or animal usage in human and veterinary medicine. Examples of such suitable excipients for the various different forms of pharmaceutical compositions described herein may be found in the "Handbook of Pharmaceutical Excipients, 2nd Edition, (1994), Edited by A Wade and P J Weller. In particular, formulations for topical delivery are described in Topical drug delivery formulations edited by David Osborne and Antonio Aman, Taylor & Francis, the complete contents of which are incorporated herein by reference. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of phydroxybenzoic acid. Antioxidants and suspending agents may be also used.

As used herein, an "effective amount" or a "therapeutically effective amount" of a peptide active agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

The term "peptide" used herein refers to a polymer composed of up to 50 amino acids, for example 5 to 50 amino acid monomers typically linked via peptide bond linkage. Peptides (including fragments and variants thereof) of and for use in the invention may be generated wholly or partly by chemical synthesis or by expression from nucleic acid. For example, the peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Illinois (1984), in M. Bodanzsky and A. 50 Bodanzsky, The Practice of Peptide Synthesis, Springer Verlag, New York (1984). When necessary, any of the peptides employed in the invention can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with NaBH4; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with NABH4. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Peptide structure modification includes the generation of retro-inverso peptides comprising the reversed sequence encoded by D-amino acids. Changes may be those that reduce susceptibility to proteolysis, reduce susceptibility to oxidation, alter binding affinity of the variant sequence (typically desirably increasing affinity), and/or confer or modify other physicochemical or functional properties on the associated variant/analog peptide The term "therapeutically effective variant" as applied to a reference peptide means peptides having an amino acid sequence that is substantially identical to the reference peptide, and which is therapeutically effective as defined below. Thus, for example, the term should be taken to include variants that are altered in respect of one or more amino acid residues. Preferably such alterations involve the insertion, addition, deletion and/or substitution of 6 or fewer amino acids, preferably 5 or fewer, 4 or fewer, even more preferably of 3 or fewer, most preferably of 1 or 2 amino acids only. Insertion, addition and substitution with natural and modified amino acids is envisaged. The variant may have conservative amino acid changes, wherein the amino acid being introduced is similar structurally, chemically, or functionally to that being substituted. Generally, the variant will have at least 50%, 60%, 70% amino acid sequence identity, preferably at least 80% sequence identity, more preferably at least 90% sequence identity, and ideally at least 95%, 96%, 97%, 98% or 99% sequence 50 identity with the parent sequence. It should be noted that any variant will have principally the same therapeutic effect, or may have enhanced effect, when tested in in vitro or in vivo models of the disease. An exemplary variant in which five of the amino acids are replaced with D-forms of the amino acids is provided as SEQUENCE ID NO: 2.

"Therapeutically effective" as applied to a peptide of the invention means a peptide that is capable of penetrating HepG2 liver cells in a hepatic cell penetration assay described herein, and significantly relieving macrovesicular steatosis in obese diabetic KKAy mice in the chronic diabetes mouse model described below. In one embodiment, a therapeutically effective peptide is capable of mediating changes in all or most of the biomarker activities listed in Table 1.

The term variant is also taken to encompass the term "fragment" and as such means a segment of amino acid SEQUENCE ID NO. 1. Typically, the fragment has between 3 and 13 contiguous amino acids in length. Generally, the fragment has a charge of −5 to +3. The charge of a peptide, fragment or region is determined using the method of Cameselle, J. C., Ribeiro, J. M., and Sillero, A. (1986). Derivation and use of a formula to calculate the net charge of acid-base compounds. Its application to amino acids, proteins and nucleotides. Biochem. Educ. 14, 131-136.

In this specification, the term "sequence identity" should be understand to comprise both sequence identity and similarity, i.e. a variant (or homolog) that shares 70% sequence identity with a reference sequence is one in which any 70% of aligned residues of the variant (or homolog) are identical to, or conservative substitutions of, the corresponding residues in the reference sequence across the entire length of the sequence. Sequence identity is the amount of characters which match exactly between two different sequences. Hereby, gaps are not counted and the measurement is relational to the shorter of the two sequences.

In terms of "sequence homology", the term should be understood to mean that a variant (or homolog) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence.

This alignment and the percent homology or sequence identity can be determined using software programs known in the art, for example, one alignment program is BLAST, using default parameters. Details of these programs can be found at the following Internet address: http://www.ncbi.nlm.nih.gov/blast/Blast.cgi.

"C-terminal domain" as applied to a fragment means the first three amino acids at the c-terminus of the fragment.

"N-terminal domain" as applied to a fragment means the last three amino acids at the n-terminus of the fragment.

"Homolog" of a reference protein should be understood to mean a protein from a different species of plant having at least 60%, 70%, 80%, 90%, 91%, 92%, 93%, 94%, 95%, 96%, 97%, 98%, 99% sequence homology with the reference protein.

"Pharmaceutical compositions": A further aspect of the invention relates to a pharmaceutical composition comprising a peptide active agent, admixed with one or more pharmaceutically acceptable diluents, excipients or carriers, or co-administered with other drugs which enhance the therapeutic effect. Even though the peptides and compositions of the present invention can be administered alone, they will generally be administered in admixture with a pharmaceutical carrier, excipient or diluent, particularly for human therapy. The pharmaceutical compositions may be for human or animal usage in human and veterinary medicine. Examples of such suitable excipients for the various different forms of pharmaceutical compositions described herein may be found in the "Handbook of Pharmaceutical Excipients, 2nd Edition, (1994), Edited by A Wade and P J Weller. In particular, formulations for topical delivery are described in Topical drug delivery formulations edited by David Osborne and Antonio Aman, Taylor & Francis, the complete contents of which are incorporated herein by reference. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of p hydroxybenzoic acid. Antioxidants and suspending agents may be also used.

The peptide or composition may be adapted for, and administered by, topical, oral, rectal, parenteral, intramuscular, intraperitoneal, intra-arterial, intrabronchial, subcutaneous, intradermal, intravenous, nasal, vaginal, buccal or sublingual routes of administration. For oral administration, particular use is made of compressed tablets, pills, tablets, gellules, drops, and capsules. Preferably, these compositions contain from 1 to 250 mg and more preferably from 10-100 mg, of active ingredient per dose. Other forms of administration comprise solutions or emulsions which may be injected intravenously, intra-arterial, subcutaneously, intradermally, intraperitoneally or intramuscularly, and which are prepared from sterile or sterilisable solutions. The pharmaceutical compositions of the present invention may also be in form of suppositories, vaginal rings, pessaries, suspensions, emulsions, lotions, ointments, creams, gels, sprays, solutions or dusting powders. The composition of the invention may be formulated for topical delivery. Topical delivery generally means delivery to the skin but can also mean delivery to a body lumen lined with epithelial cells, for example the lungs or airways, the gastrointestinal tract, the buccal cavity. In particular, formulations for topical delivery are described in Topical drug delivery formulations edited by David Osborne and Antonio Aman, Taylor & Francis, the complete contents of which are incorporated herein by reference. Compositions or formulations for delivery to the airways are described in O'Riordan et al (Respir Care, 2002, November 47), EP2050437, WO2005023290, US2010098660, and US20070053845. Composition and formulations for delivering active agents to the iluem, especially the proximal iluem, include microparticles and microencapsulates where the active agent is encapsulated within a protecting matrix formed of polymer or dairy protein that is acid resistant but prone to dissolution in the more alkaline environment of the ileum. Examples of such delivery systems are described in EP1072600.2 and EP13171757.1. An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention. Depending upon the need, the agent may be administered at a dose of from 0.01 to 30 mg/kg body weight, such as from 0.1 to 10 mg/kg, more preferably from 0.1 to 1 mg/kg body weight. In an exemplary embodiment, one or more doses of 10 to 300 mg/day or more preferably, 10 to 150 mg/day, will be administered to the patient for the treatment of an inflammatory disorder.

In a particularly preferred embodiment, the methods and uses of the invention involve administration of a peptide or composition in combination with one or more other active agents, for example, existing NAFLD drugs or pharmacological enhancers available on the market. In such cases, the compounds of the invention may be administered consecutively, simultaneously or sequentially with the one or more other active agents.

In one embodiment of the invention, the peptide active agent may be administered in the form of a conjugate comprising the peptide, a linker, and an antibody molecule (or antibody fragment) intended to increase the half-life of the conjugate in-vivo.

"Modified peptides": In one embodiment, the peptides of the invention (including peptide variants) may be a modified peptide. The term "modified peptide" is used interchangeably with the term derivative of the peptide. In one embodiment, the term "modified peptide" means a peptide that is modified to exhibit one or more of the following properties compared with the unmodified peptide: increase plasma half-life; increase the lipophilicity of the peptide; increase the renal clearance of the modified peptide; and increase the resistance of the modified peptide to proteolytic degradation, while typically retaining the rpS6 phosphorylation activity. Various methods of modifying a peptide of the invention to exhibit these properties are disclosed herein, including conjugating the peptide with a binding partner (for example an albumin binding small molecule, large polymer, long life plasma protein, or antibody or antibody-fragment), cyclisation, addition of N- or C-terminal, or side chain, protecting groups, replacing L-amino acids with D-isomers, amino acid modification, increased plasma protein binding, increased albumin binding The modified peptide includes but is not limited to a peptide which has been substituted with one or more groups as defined herein, or conjugated with a binding partner, or cyclized. Generally, the peptide is modified to increase it half-life in-vivo in an animal. Various methods of modification are provided below.

In one embodiment, the modification may be any modification that provides the peptides and or the composition of the invention with an increased ability to penetrate a cell. In one embodiment, the modification may be any modification that increases the half-life of the composition or peptides of the invention. In one embodiment, the modification may be any modification that increases activity of the composition or peptides of the invention. In one embodiment, the modification may be any modification that increases selectivity of the composition or peptides of the invention.

In one embodiment, the group is a protecting group. The protecting group may be an N-terminal protecting group, a C-terminal protecting group or a side-chain protecting group. The peptide may have one or more of these protecting groups.

The person skilled in the art is aware of suitable techniques to react amino acids with these protecting groups. These groups can be added by preparation methods known in the art, for example the methods as outlined in paragraphs [0104] to [0107] of US2014120141. The groups may remain on the peptide or may be removed. The protecting group may be added during synthesis.

In an embodiment of the invention the peptides may be substituted with a group selected from one or more straight chain or branched chain, long or short chain, saturated, or unsaturated, substituted with a hydroxyl, amino, amino acyl, sulfate or sulphide group or unsubstituted having from 1 to 29 carbon atoms. N-acyl derivatives include acyl groups derived from acetic acid, capric acid, lauric acid, myristic acid, octanoic acid, palmitic acid, stearic acid, behenic acid, linoleic acid, linolenic acid, lipoic acid, oleic acid, isosteric acid, elaidoic acid, 2-ethylhexaneic acid, coconut oil fatty acid, tallow fatty acid, hardened tallow fatty acid, palm kernel fatty acid, lanolin fatty acid or similar acids. These may be substituted or unsubstituted. When substituted they are preferably substituted with hydroxyl, or sulphur containing groups such as but not limited to SO3H, SH, or S—S.

In an embodiment of the current invention, the peptide is R1-X— R2.
R1 and/or R2 groups respectively bound to the amino-terminal (N-terminal) and carboxyl-terminal (C-terminal) of the peptide sequence.

In one embodiment, the peptide is R1-X. Alternatively, the peptide is X— R2.

Preferably, R1 is H, C1-4 alkyl, acetyl, benzoyl or trifluoroacetyl;
X is the peptide of the invention;
R2 is OH or NH2.

In an embodiment, R 1 is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl, Tert-butyloxycarbonyl, 9-fluorenylmethyloxycarbonyl (Fmoc) and R5-CO—, wherein R5 is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl; R2 is selected from the group formed by —NR3R4, —OR3 and —SR3, wherein R3 and R4 are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that R1 and R2 are not α-amino acids.

In accordance with another preferred embodiment, R2 is —NR3R4, —OR 3 or —SR 3 wherein R3 and R4 are independently selected from the group formed by H, substituted or 50 unsubstituted C 1-C 24 alkyl, substituted or unsubstituted C2-C 24 alkenyl, Tert-butyloxycarbonyl, 9-fluorenylmethyloxycarbonyl (Fmoc), substituted or unsubstituted C2-C 24 alkynyl, substituted or unsubstituted C3-C 24 cycloalkyl, substituted or unsubstituted C 5-C 24 cycloalkenyl, substituted or unsubstituted C8-C 24 cycloalkynyl, substituted or unsubstituted C 6-C 30 aryl, substituted or unsubstituted C7-C24 aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, R 3 and R 4 can be bound by a saturated or unsaturated carbon-carbon bond, forming a cycle with the nitrogen atom. More preferably R 2 is —NR3R4 or —OR 3, wherein R3 and R4 are independently selected from the group formed by H, substituted or unsubstituted C1-C 24 alkyl, substituted or unsubstituted C2-C24 alkenyl, substituted or unsubstituted C2-C24 alkynyl, substituted or unsubstituted C3-C10 cycloalkyl, substituted or unsubstituted C6-C 15 aryl and substituted or unsubstituted heterocyclyl of 3-10 members, substituted or unsubstituted heteroarylalkyl with a ring of 3 to 10 members and an alkyl chain of 1 to 6 carbon atoms. More preferably R3 and R4 are selected from the group formed by H, methyl, ethyl, hexyl, dodecyl, or hexadecyl. Even more preferably R3 is H and R4 is selected from the group formed by H, methyl, ethyl, hexyl, dodecyl, or hexadecyl. In accordance with an even more preferred embodiment, R2 is selected from —OH and —NH2.

In accordance with another embodiment of this invention R 1 is selected from the group formed by H, acetyl, lauroyl, myristoyl or palmitoyl, and R2 is —NR3R 4 or —OR3 wherein R3 and R4 are independently selected from H, methyl, ethyl, hexyl, dodecyl and hexadecyl, preferably R2 is —OH or —NH2. More preferably, R1 is acetyl or palmitoyl and R2 is —NH2. In a preferred embodiment, the acyl group is bound to the N-terminal end of at least one amino acid of the peptide.

In an embodiment of the invention, the peptide is modified to comprise a side chain protecting group. The side chain protecting group may be one or more of the group comprising benzyl or benzyl based groups, t-butyl-based groups, benzyloxy-carbonyl (Z) group, and allyloxycarbonyl (alloc) protecting group. The side chain protecting group may be derived from an achiral amino acid such as achiral glycine. The use of an achiral amino acid helps to stabilise the resultant peptide and also facilitate the facile synthesis route of the present invention. Preferably, the peptide further comprises a modified C-terminus, preferably an amidated C-terminus. The achiral residue may be alpha-aminoisobutyric acid (methylalaine). It will be appreciated that the specific side chain protecting groups used will depend on the sequence of the peptide and the type of N-terminal protecting group used.

In one embodiment of the invention the peptide is conjugated, linked or fused to one or more polyethylene glycol polymers or other compounds, such as molecular weight increasing compounds. The molecular weight increasing compound is any compound that will increase the molecular weight, typically by 10% to 90%, or 20% to 50% of the resulting conjugate and may have a molecular weight of between 200 and 20,000, preferably between 500 and 10,000. The molecular weight increasing compound may be PEG, any water-soluble(amphiphilic or hydrophilic) polymer moiety, homo or co-polymers of PEG, a monomethyl-substituted polymer of PEG (mPEG) and polyoxyethylene glycerol (POG), polyamino acids such as poly-lysine, poly-glutamic acid, poly-aspartic acid, particular those of L conformation, pharmacologically inactive proteins such as albumin, gelatin, a fatty acid, polysaccharide, a lipid amino acid and dextran. The polymer moiety may be straight chained or branched and it may have a molecular weight of 500 to 40000 Da, 5000 to 10000 Da, 10000 to 5000, Da. The compound may be any suitable cell penetrating compound, such as tat peptide, penetratin, pep-1. The compound may be an antibody molecule. The compound may be a lipophilic moiety or a polymeric moiety.

The lipophilic substituent and polymeric substituents are known in the art. The lipophilic substituent includes an acyl group, a sulphonyl group, an N atom, an O atom or an S atom which forms part of the ester, sulphonyl ester, thioester, amide or sulphonamide. The lipophilic moiety may include a hydrocarbon chain having 4 to 30 C atoms, preferably between 8 and 12 C atoms. It may be linear or branched, saturated or unsaturated. The hydrocarbon chain may be further substituted. It may be cycloalkane or heterocycloalkane. The peptide may be modified at the N-terminal, C-terminal or both. The polymer or compound is preferably linked to an amino, carboxyl or thio group and may be linked by N-termini or C-termini of side chains of any amino acid residue. The polymer or compound may be conjugated to the side chain of any suitable residue.

The polymer or compound may be conjugated via a spacer. The spacer may be a natural or unnatural amino acid, succinic acid, lysyl, glutamyl, asparagyl, glycyl, beta-alanyl, gamma-amino butanoyl. The polymer or compound may be conjugated via an ester, a sulphonyl ester, a thioester, an amide, a carbamate, a urea, a sulphonamide. A person skilled in the art is aware of suitable means to prepare the described conjugate.

Peptides can be chemically modified by covalent conjugation to a polymer to increase their circulating half-life, for example. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties.

The peptides of the invention may be subjected to one or more modifications for manipulating storage stability, pharmacokinetics, and/or any aspect of the bioactivity of the peptide, such as, e.g., potency, selectivity, and drug interaction. Chemical modification to which the peptides may be subjected includes, without limitation, the conjugation to a peptide of one or more of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide co-polymer, polypropylene glycol, polyoxyethylated polyols (e.g., glycerol) and polyvinyl alcohol, colominic acids or other carbohydrate based polymers, polymers of amino acids, and biotin derivatives. PEG conjugation of proteins at Cys residues is disclosed, e.g., in Goodson, R. J. & Katre, N. V. (1990) Bio/Technology 8, 343 and Kogan, T. P. (1992) Synthetic Comm. 22, 2417.

Modified peptides also can include sequences in which one or more residues are modified (i.e., by phosphorylation, sulfation, acylation, PEGylation, etc.), and mutants comprising one or more modified residues with respect to a parent sequence. Amino acid sequences may also be modified with a label capable of providing a detectable signal, either directly or indirectly, including, but not limited to, radioisotope, fluorescent, and enzyme labels. Fluorescent labels include, for example, Cy3, Cy5, Alexa, BODIPY, fluorescein (e.g., FluorX, DTAF, and FITC), rhodamine (e.g., TRITC), auramine, Texas Red, AMCA blue, and Lucifer Yellow. Preferred isotope labels include 3H, 14C, 32 P, 35S, 36Cl, 51Cr, 57Co, 58Co, 59Fe, 90Y, 125I, 131I, and 286Re. Preferred enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.).

In an embodiment, the peptide, variant and/or composition is modified to increase drug performance ability. In an embodiment, the peptide, variant and/or composition is modified to increase stability, permeability, maintain potency, avoid toxicity and/or to increase half-life. The modification may be as described above. For example, the modification may be to protect the N and C-terminus, it may be a modified amino acid, cyclisation, replacement of an amino acid, and/or conjugation to macromolecules or large polymers or long life plasma proteins. Strategies to extend a half-life may be as described by Strohl, et al (BioDrugs, 2015), Schlapschy, et al (Protein Eng Des Sel. 2013), Podust, V N, et al (Protein Eng Des Sel. 2013), Zhang, L et al (Curr Med Chem. 2012), Gaberc-Porekar, V, et al (Curr Opin Drug Discov Devel. 2008). Examples include using PEGylation, lipidation (covalent binding of fatty acids to peptide side chains), fusion to Fc domains and human serum albumin, fusion with a hydrophilic amino acid polymer, e.g. XTEN or PAS, and/or fusion with half-life extension proteins.

Modification of peptides to extend the in-vivo half-life of the peptide is described in the literature, for example:

Strategies to improve plasma half life time of peptide and protein drugs. Werle M, Bernkop-Schniarch A. Amino Acids. 2006 June; 30(4):351-67.

Due to the obvious advantages of long-acting peptide and protein drugs, strategies to prolong plasma half life time of such compounds are highly on demand. Short plasma half life times are commonly due to fast renal clearance as well as to enzymatic degradation occurring during systemic circulation. Modifications of the peptide/protein can lead to prolonged plasma half life times. By shortening the overall amino acid amount of somatostatin and replacing L: —analogue amino acids with D: —amino acids, plasma half life time of the derivate octreotide was 1.5 hours in comparison to only few minutes of somatostatin. A PEG(2.40 K) conjugate of INF-alpha-2b exhibited a 330-fold prolonged plasma half life time compared to the native protein. It was the aim of this review to provide an overview of possible strategies to prolong plasma half life time such as modification of N- and C-terminus or PEGylation as well as methods to evaluate the effectiveness of drug modifications. Furthermore, fundamental data about most important proteolytic enzymes of human blood, liver and kidney as well as their cleavage specificity and inhibitors for them are provided in order to predict enzymatic cleavage of peptide and protein drugs during systemic circulation.

Strategic Approaches to Optimizing Peptide ADME Properties. Li Di AAPS J. 2015 January; 17(1): 134-143.

Strategies to Stabilize Peptides from Proteolysis

Many approaches are available to enhance stability of peptides through structure modification. Some approaches not only improve stability, but also enhance other ADME properties, e.g., cyclization can increase stability and permeability; conjugation to macromolecules can improve stability and reduce renal clearance. It is important to maintain potency and avoid toxicity while improving stability and ADME properties of peptides.

Protecting N- and C-terminus

A number of proteolytic enzymes in blood/plasma, liver or kidney are exopeptidases, aminopeptidases and carboxypeptidases and they break down peptide sequences from the N- and C-termini. Modification of the N- or/and C-termini can often improve peptide stability. Many examples have reported that N-acetylation, and C-amidation increase resistance to proteolysis.

Replacing L-Amino Acids with D-Amino Acids

Substituting natural L-amino acids with nonnatural D-amino acids decreases the substrate recognition and binding affinity of proteolytic enzymes and increases stability. One example 50 is vasopressin, which contains an L-Arg and has a half-life of 10-35 min in humans. The D-Arg analog, desmopressin, has a half-life of 3.7 h in healthy human volunteers. In the study of a bicyclic peptide inhibitor of the cancer-related protease urokinase-type plasminogen activator (uPA), replacement of a specific glycine with a D-serine not only improves potency by 1.8-fold but also increases stability by 4-fold in mouse plasma.

Modification of Amino Acids

Modification of natural amino acids can improve the stability of peptides by introducing steric hindrance or disrupting enzyme recognition. For example, gonadotropin-releasing hormone has a very short half-life (minutes), while buserelin, in which one Gly is replaced with a t-butyl-D-Ser and another Gly is substituted by ethylamide, has a much longer half-life in humans.

Cyclization

The peptide of the invention may be cyclised. Cyclization introduces conformation constraint, reduces the flexibility of peptides, and increases stability and permeability. Depending on the functional groups, peptides can be cyclized head-to-tail, head/tail-to-side-chain, or side-chain-to-side-chain. Cyclization is commonly accomplished through lactamization, lactonization, and sulfide-based bridges. Disulfide bridges create folding and conformational constraints that can improve potency, selectivity, and stability. A number of disulfide bond-rich peptides are on the market or in preclinical or clinical development, e.g., linaclotide, lepirudin, and ziconotide. In one embodiment, the peptide is cyclised between between amino and carboxy ends of the peptide. In one embodiment, the peptide is cyclised between an amino end and a side chain. In one embodiment, the peptide is cyclised between a carboxy end and a side chain. In one embodiment, the peptide is cyclised between side chains. In one embodiment, the cyclic peptide is selected from a homodetic cyclic peptide, a cyclic isopeptide, a cyclic depsipeptide, or a monocyclic or bicyclic peptide. Methods of cyclisation of peptides are described in the following:

Jensen, Knud (2009-09-01). Peptide and Protein Design for Biopharmaceutical Applications. John Wiley & Sons. ISBN 9780470749715.

Wenyan, Xu; Jun, Tang; Changjiu, Ji; Wenjun, He; Ninghua, Tan (2008). "Application of a TLC chemical method to detection of cyclotides in plants". Science Bulletin. 53 (11): 1671-1674. doi:10.1007/s11434-008-0178-8.

Borthwick A D (May 2012). "2,5-Diketopiperazines: Synthesis, Reactions, Medicinal Chemistry, and Bioactive Natural Products". Chemical Reviews. 112 (7): 3641-3716. doi:10.1021/cr200398y. PMID 22575049.

Barber, Carla J. S.; Pujara, Pareshkumar T.; Reed, Darwin W.; Chiwocha, Shiela; Zhang, Haixia; Covello, Patrick S. (2013). "The Two-step Biosynthesis of Cyclic Peptides from Linear Precursors in a Member of the Plant Family Caryophyllaceae Involves Cyclization by a Serine Protease-like Enzyme". Journal of Biological Chemistry. 288 (18): 12500-12510. doi:10.1074/jbc.M112.437947. PMC 3642298. PMID 23486480.

Wenyan Xu; et al. (2011). "Various mechanisms in cyclopeptide production from precursors synthesized independently of non-ribosomal peptide synthetases". Acta Biochimica et Biophysica Sinica. 43 (10): 757-762. doi: 10.1093/abbs/gmr062. PMC 3180235. PMID 21764803.

Wenyan Xu; et al. "Plant Cyclopeptides and Possible Biosynthetic Mechanisms".

David J. Craik (17 Mar. 2006). "Seamless Proteins Tie Up Their Loose Ends". Science. 311 (5767): 1563-7. doi: 10.1126/science.1125248. PMID 16543448.

Conjugation to Macromolecules

Conjugation to macromolecules (e.g., polyethylene glycol (PEG), albumin) is an effective strategy to improve stability of peptides and reduce renal clearance.

Renal Clearance

Many peptides exhibit promising in vitro pharmacological activity but fail to demonstrate in 50 vivo efficacy due to very short in vivo half-life (minutes). The rapid clearance and short half-life of peptides hamper their development into successful drugs. The main causes of rapid clearance of peptides from systemic circulation are enzymatic proteolysis or/and renal clearance. The glomeruli have a pore size of ~8 nm, and hydrophilic peptides with MW<2-25 kDa are susceptible to rapid filtration through the glomeruli of the kidney. Since peptides are not easily reabsorbed through the renal tubule, they frequently have high renal clearance and short half-life. Other minor routes of peptide clearance are endocytosis and degradation by proteasome and the liver.

Comparison between systemic and renal clearance in animal models provides useful information on whether renal clearance is likely to be a major elimination pathway.

For renal-impaired patients, dose adjustment may be needed for peptide drugs to avoid accumulation and higher drug exposure, as inappropriate dosing in patients with renal dysfunction can cause toxicity or ineffective therapy. Several strategies have been developed to reduce peptide renal clearance and prolong half-life. These will be reviewed next.

Increase Plasma Protein Binding

Renal clearance of peptides is reduced when they are bound to membrane proteins or serum proteins. An example is the cyclic peptide drug octreotide, a treatment for endocrine tumors, which has about 100 min half-life in humans due to binding to lipoproteins (fraction unbound 0.65)

Covalent Linkage to Albumin-Binding Small Molecules

Covalently attaching albumin-binding small molecules to peptides can reduce glomerular filtration, improve proteolytic stability, and prolong half-life by indirectly interacting with albumin through the highly bound small molecules.

Conjugation to Large Polymers

Conjugation of peptides to large synthetic or natural polymers or carbohydrates can increase their molecular weight and hydrodynamic volume, thus reducing their renal clearance. The common polymers used for peptide conjugation are PEG, polysialic acid (PSA), and hydroxyethyl starch (HES).

Fusion to Long-Live Plasma Proteins

Plasma proteins, such as albumin and immunoglobulin (IgG) fragments, have long half-lives of 19-21 days in humans. Because of the high MW (67-150 kDa), these proteins have low renal clearance, and their binding to neonatal Fc receptor (FcRn) reduces the elimination through pinocytosis by the vascular epithelium. Covalent linkage of peptides to albumin or IgG fragments can reduce renal clearance and prolong half-life.

Fusion Proteins for Half-Life Extension of Biologics as a Strategy to Make Biobetters William R. Strohl BioDrugs. 2015; 29(4): 215-239.

Schlapschy, M, Binder, U, Borger, C et al. PASYlation: a biological alternative to PEGylation for extending the plasma half-life of pharmaceutically active proteins. Protein Eng Des Sel. 2013; 26(8):489-501.

Podust, V N, Sim, B C, Kothari, D et al. Extension of in vivo half-life of biologically active peptides via chemical conjugation to XTEN protein polymer. Protein Eng Des Sel. 2013; 26(11):743-53.

Zhang, L, Bulaj, G. Converting Peptides into Drug Leads by Lipidation. Curr Med Chem. 2012; 19(11):1602-18.

Gaberc-Porekar, V, Zore, I, Podobnik, B et al. Obstacles and pitfalls in the PEGylation of therapeutic proteins. Curr Opin Drug Discov Devel. 2008; 11(2):242-50.

By Dr Ronald V. Swanson—Long live peptides evolution of peptide half-life extension technologies and emerging hybrid approaches. From Drug Discovery World on line. Spring 2014

PEGylation

The attachment of long chains of the hydrophilic polymer polyethylene glycol to molecules of interest, PEGylation was originally conceived as a modification to prevent the recognition of foreign proteins by the immune system and, thereby, enable their utility as therapeutics. Once formed, antibodies against unmodified drugs can rapidly neutralise and clear protein drugs. Unexpectedly, PEGylation improved the pharmacokinetics of the proteins even in the absence of anti-drug antibodies1. Simply by making drug molecules larger, PEGylation led to the drug being filtered more slowly by the kidneys. The empirical observation that increasing size or hydrodynamic radius led to reduced renal clearance and increased half-life then became the dominant rationale for the PEGylation of protein and peptide drugs. PEGylation can have a variety of effects on the molecule including making proteins or peptides more water-soluble and protecting them from degradation by proteolytic enzymes. PEGylation can also impact the binding of therapeutic proteins to their cognate cellular receptors, usually reducing the affinity. Changes in the size, structure and attachment mode of PEG polymers can affect the biological activity of the attached drug.

The first-generation PEGylation methods were filled with challenges. However, the chemistry of PEGylation is quite simple. The process involves the covalent attachment of polyethylene glycol chains to reactive side chains of a protein or peptide. For example, PEG is easily attached to the -amino groups of lysine on the surface of proteins or peptides2. The reaction is pH-dependent. At high pH (8.0 or higher), lysine side chain amino groups are covalently attached to PEG through N-hydroxy succinimides. This method typically results in a family of products containing different numbers of PEG chains attached at different sites on a protein rather than a single discrete product3. The first approved PEGylated pharmaceuticals were Pegademase bovine (PEGylated bovine adenosine deamidase) as enzyme replacement therapy for severe combined immunodeficiency and Pegaspargase (PEGylated asparaginase) for treatment of acute lymphoblastic leukaemia1. These drugs were complex mixtures of various PEGylated species, but with improved properties for therapy over native enzymes, including increased serum half-life and decreased immunogenicity of the proteins. Due to the inherent polydispersity of the PEG, quality and batch-to-batch reproducibility was difficult. Despite this limitation, two PEGylated interferons, (Peginterferon alfa-2b and Peginterferon alfa-2a) that are heterogeneous populations of numerous mono-PEGylated positional isomers, have been FDA-approved for the treatment of hepatitis C. These drugs were brought to market in 2001 and 2002, respectively.

A variety of enhancements and variations have been made to the fundamental PEGylation technology. Second-generation PEGylation processes introduced the use of branched structures as well as alternative chemistries for PEG attachment. In particular, PEGs with cysteine reactive groups such as maleimide or iodoacetamide allow the targeting of the PEGylation to a single residue within a peptide or protein reducing the heterogeneity of the final product but not eliminating it due to the polydispersity of the PEG itself.

While the original rationale for PEGylation was to reduce immunogenicity; nevertheless, there have been a few examples of immunogenic PEGylated proteins. One example is PEGylated urate oxidase, an enzyme that lowers the plasma urate level in patients with gout. In clinical trials, a relatively high percentage of patients with gout did not respond to the therapy and developed antibodies that were specific for PEG, but not for the uricase protein2. PEGylated liposomes, also generally thought to be non-immunogenic, have been found to be immunogenic in some studies. PEGylated liposomes elicit a strong anti-PEG immunoglobulin M (IgM) response. In addition, multiple injections of PEG-glucuronidase were shown to elicit the generation of specific anti-PEG IgM antibodies, thus accelerating the clearance of PEG-modified proteins from the body.

A major potential drawback of using PEG as a modifier is that it is non-biodegradable. The US Food and Drug Administration (FDA) has approved PEG for use as a vehicle in pharmaceuticals, including injectable, topical, rectal and nasal formulations. PEG shows little toxicity and is eliminated from the body intact by either the kidneys (for PEGs <30 kDa) or in the feces (for PEGs >20 kDa)1. Repeated administration of some PEGylated proteins to animals has resulted in observations of renal tubular cellular vacuolation. Recently, vacuolation of choroid plexus epithelial cells has also been seen in toxicity studies with proteins conjugated with large (≥40 kDa) PEGs. The choroid plexus epithelial cells produce cerebrospinal fluid and form the blood CSF barrier. The long-term negative consequences of cellular vacuolation are unclear, but it does represent an undesirable consequence for some potential therapeutics. One possible alternative would be substitution of a biodegradable polymer in place of PEG. Polymers, such as hydroxyethyl starch (HES) are a possible alternative. HES is non-toxic and biodegradable and used as a blood expander. A process of HESylation would function similarly to PEGylation in reducing renal clearance through increasing a peptide's hydrodynamic radius but may confer a lower propensity for accumulation due to biodegradability. However, HES and other proposed biodegradable polymer PEG alternatives are, like PEG, polydisperse making characterisation of the final product and metabolites difficult. One emerging solution which mitigates both concerns is to use defined polypeptides as the polymer component; this approach will be discussed later in the article.

Lipidation

A second major chemical modification method to increase peptide half-life is lipidation which involves the covalent binding of fatty acids to peptide side chains4. Originally conceived of and developed as a method for extending the half-life of insulin, lipidation shares the same basic mechanism of half-life extension as PEGylation, namely increasing the hydrodynamic radius to reduce renal filtration. However, the lipid moiety is itself relatively small and the effect is mediated indirectly through the non-covalent binding of the lipid moiety to circulating albumin. A large (67 KDa) and highly abundant protein in human serum (35-50 g/L), albumin naturally functions to transport molecules, including lipids, throughout the body. Binding to plasma proteins can also protect the peptide from attacks by peptidases through steric hindrance, again akin to what is seen with PEGylation. One consequence of lipidation is that it reduces the water-solubility of the peptide but engineering of the linker between the peptide and the fatty acid can modulate this, for example by the use of glutamate or mini PEGs within the linker. Linker engineering and variation of the lipid moeity can affect self-aggregation which can contribute to increased half-life by slowing down biodistribution, independent of albumin5.

Following the pioneering work with insulin6, lipidation of a variety of peptides has been explored, particularly peptides within the diabetes space including human glucagon-like peptide-1 (GLP-1) analogues, glucose-dependent insulinotropic polypeptide and GLP-1R/Glucagon receptor coagonists among others. Two lipidated peptide drugs are currently FDA-approved for use in humans. These are both long-acting anti-diabetics, the GLP-1 analogue liraglutide and insulin detemir.

A potentially pharmacologically-relevant difference between PEGylation and lipidation is that the therapeutically active peptide is covalently linked to the much larger PEG, whereas the smaller fatty acyl-peptide conjugate is non-covalently associated with the larger albumin, bound and unbound forms existing in equilibrium. This can result in differences in biodistribution that may result in different pharmacology as access to receptors localised in different tissues may elicit differential effects. In some cases, more restricted biodistribution may be desirable, while in others, greater tissue penetration may be important. An interesting variation of the PEG approach which addresses this issue has been developed by Santi et al in which releasable PEG conjugates with predictable cleavage rates are utilised7.

PEGylation and lipidation both confer protection against proteases and peptidases by shielding through steric hindrance and extend circulating half-life through increased hydrodynamic radius, directly or indirectly. Both methods utilise chemical conjugation and are flexible in that they are agnostic to the means used to generate the peptide they are modifying, whether biologically or synthetically produced. An advantage of using synthetic peptides is that they can incorporate non-natural amino acids designed to address a number of specific issues including instability due to known proteolytic cleavage liabilities. They can also be more flexible in terms of the choice of attachment site which is critical if activity or potency is highly dependent on the free termini or a modified residue such as a Cterminal amide.

Classical Genetic Fusions: Fc and HSA

Classical genetic fusions to long-lived serum proteins offer an alternative method of half-life extension distinct from chemical conjugation to PEG or lipids. Two major proteins have traditionally been used as fusion partners: antibody Fc domains and human serum albumin (HAS). Fc fusions involve the fusion of peptides, proteins or receptor exodomains to the Fc portion of an antibody. Both Fc and albumin fusions achieve extended half-lives not only by increasing the size of the peptide drug, but both also take advantage of the body's natural recycling mechanism: the neonatal Fc receptor, FcRn. The pH-dependent binding of these proteins to FcRn prevents degradation of the fusion protein in the endosome. Fusions based on these proteins can have half-lives in the range of 3-16 days, much longer than typical PEGylated or lipidated peptides. Fusion to antibody Fc can improve the solubility and stability of the peptide or protein drug. An example of a peptide Fc fusion is dulaglutide, a GLP-1 receptor agonist currently in late-stage clinical trials. Human serum albumin, the same protein exploited by the fatty acylated peptides is the other popular fusion partner. Albiglutide is a GLP-1 receptor agonist based on this platform. A major difference between Fc and albumin is the dimeric nature of Fc versus the monomeric structure of HAS leading to presentation of a fused peptide as a dimer or a monomer depending on the choice of fusion partner. The dimeric nature of a peptide Fc fusion can produce an avidity effect if the target receptors are spaced closely enough together or are themselves dimers. This may be desirable or not depending on the target.

Designed Polypeptide Fusions: XTEN and PAS

An intriguing variation of the recombinant fusion concept has been the development of designed lowcomplexity sequences as fusion partners, basically unstructured, hydrophilic amino acid polymers that are functional analogs of PEG. The inherent biodegradability of the polypeptide platform makes it attractive as a potentially more benign alternative to PEG. Another advantage is the precise molecular structure of the recombinant molecule in contrast to the polydispersity of PEG. Unlike HSA and Fc peptide fusions, in which the three-dimensional folding of the fusion partner needs to be maintained, the recombinant fusions to unstructured partners can, in many cases, be subjected to higher temperatures or harsh conditions such as HPLC purification.

The most advanced of this class of polypeptides is termed XTEN (Amunix) and is 864 amino acids long and comprised of six amino acids (A, E, G, P, S and T). Enabled by the biodegradable nature of the polymer, this is much larger than the 40 KDa PEGs typically used and confers a concomitantly greater half-life extension. The fusion of XTEN to peptide drugs results in half-life extension by 60- to 130-fold over native molecules. Two fully recombinantly produced XTENylated products have entered the clinic, namely VRS-859 (Exenatide-XTEN) and VRS-317 (human growth hormone-XTEN). In Phase la studies, VRS-859 was found to be well-tolerated and efficacious in patients with Type 2 diabetes. 50 VRS-317 reported superior pharmacokinetic and pharmacodynamic properties compared with previously studied rhGH products and has the potential for once-monthly dosing.

A second polymer based on similar conceptual considerations is PAS (XL-Protein GmbH)9. A random coil polymer comprised of an even more restricted set of only three small uncharged amino acids, proline, alanine and serine. Whether differences in the biophysical properties of PAS and the highly negatively charged XTEN may contribute to differences in biodistribution and/or in vivo activity is yet unknown but will be revealed as these polypeptides are incorporated into more therapeutics and the behaviour of the fusions characterised.

All the peptide protein fusions, whether the partner is Fc, HSA, XTEN or PAS, are genetically encoded and consequently suffer from similar constraints. One limitation is that only naturally occurring amino acids are incorporated, unlike the methods employing chemical conjugation which allow the use of synthetic peptides incorporating non-natural amino acids. Although methods to overcome this by expanding the genetic code are being developed by companies such as Ambrx or Sutro, they are not yet in wide use. A second limitation is that either the N- or C-terminus of the peptide needs to be fused to the partner. Oftentimes, the peptide termini are involved in receptor interactions and genetic fusion to one or both termini can greatly impair activity. Since the site of PEG or lipid conjugation can be anywhere on the peptide, it can be optimised to maximise biological activity of the resulting therapeutic.

Hybrid methods merging synthetic peptides with half-life extension proteins.

While genetic fusions have historically offered the potential for greater half-life extension, they lack the advantages afforded by the methods utilising chemical conjugation, PEGylation and lipidation, in terms of flexibility of attachment sites and incorporation of unnatural amino acids or modifications to the peptide backbone. One of the first efforts to merge the advantages of the genetic fusions with chemical conjugation for half-life extension was carried out by researchers at the Scripps Research Institute in La Jolla with the technology which later formed the basis for the biotech company CovX10,11. Using a catalytic aldolase antibody, these researchers developed a platform through which the active site lysine of the antibody forms a reversible covalent enamine bond with a beta-diketone incorporated into a peptide or small molecule. The resulting complex is termed a CovXBody™. This approach combines the functional qualities of a peptide drug or small molecule with the long serum half-life of an antibody, not through a genetic fusion but rather through a chemical linkage. Following the initial demonstration of the technology, researchers expanded upon the use of CovX-Body™ prototype that is based on an integrin targeting peptidomimetic pharmacophore. At least three molecules based on this architecture have entered clinical development: CVX-096, a Glp-1R agonist; CVX-060, an Angiopoietin-2 binding peptide; and CVX-045, a thrombospondin mimetic.

Recently, the XTEN polypeptide has also been used in a chemical conjugation mode12 making it even more directly analogous to PEG. The first example of an XTENylated peptide that was created using this method is GLP2-2G-XTEN in which the peptide is chemically conjugated to the XTEN protein polymer using maleimide-thiol chemistry. The chemically conjugated GLP2-2GXTEN molecules exhibited comparable in vitro activity, in vitro plasma stability and pharmacokinetics in rats comparable to recombinantly-fused GLP2-2G-XTEN.

The number and spacing of reactive groups such as lysine or cysteine side chains in the completely designed sequences of XTEN or PAS polypeptides can be precisely controlled through site-directed changes due to the restricted amino acid sets from which they are composed. This provides an additional degree of flexibility over methods which might utilise Fc or albumin whose sequences naturally contain many reactive groups and stands in contrast to the CovX technology which relies on a reactive residue in a highly specialised active site. In addition, the lack of tertiary structure of XTEN or PAS should provide more 50 flexibility over the conditions and chemistries used in coupling and in the purification of conjugates.

In summary, hybrid peptide half-life extension methods are emerging that combine the advantages and overcome the individual limitations of chemical conjugation and genetic fusions methods. These methods enable the creation of molecules based on recombinant polypeptide-based partners that impart longer half-life but free the therapeutic peptide moieties from the limitations of being composed solely of natural L-amino acids or configured solely as linear, unidirectional polypeptides fused at either the N- or C-terminus, thus opening the door to a wide range of longer acting peptide-based drugs.

As used herein, the term "expression vector of the invention" may be any suitable vector, including chromosomal, non-chromosomal, and synthetic nucleic acid vectors (a nucleic acid sequence comprising a suitable set of expression control elements) suitable for expression of a peptide of the invention in a cell. Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, the peptide-encoding nucleic acid molecule is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. Nos. 5,589,466 and 5,973,972). In one embodiment, the DNA comprises an expression control sequence.

In one embodiment, the vector is suitable for expression of a polyamino acid sequence of the invention in a bacterial cell. Examples of such vectors include expression vectors such as BlueScript (Stratagene), pIN vectors (Van Heeke & Schuster, 1989, J Biol Chem 264, 5503-5509), pET vectors (Novagen, Madison, Wis.) and the like. In one embodiment, the expression vector may also or alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed., 1987, Current Protocols in Molecular Biology, Greene Publishing and Wiley InterScience New York; and Grant et al., 1987, Methods in Enzymol 153, 516-544). In other embodiments, the expression vector is suitable for expression in baculovirus-infected insect cells. (Kost, T; and Condreay, J P, 1999, Current Opinion in Biotechnology 10 (5): 428-33.)

Expression control sequences are engineered to control and drive the transcription of genes of interest, and subsequent expression of proteins in various cell systems. Plasmids combine an expressible gene of interest with expression control sequences (i.e. expression cassettes) that comprise desirable elements such as, for example, promoters, enhancers, selectable markers, operators, etc. In an expression vector of the invention, polyamino acid sequence-encoding nucleic acid molecules may comprise or be associated with any suitable promoter, enhancer, selectable marker, operator, repressor protein, polyA termination sequences and other expression-facilitating elements.

"Promoter" as used herein indicates a DNA sequence sufficient to direct transcription of a DNA sequence to which it is operably linked, i.e., linked in such a way as to permit transcription of the polyamino acid sequence-encoding nucleotide sequence when the appropriate signals are present. The expression of a polyamino acid sequence-encoding nucleotide sequence may be placed under control of any promoter or enhancer element known in the art. Examples of such elements include strong expression promoters (e.g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters). In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules of the invention may also be operably linked to an effective poly (A) termination sequence, an origin of replication for plasmid product in E. coli, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. Under the selective conditions, only cells that express the appropriate selectable marker can survive. Commonly, selectable marker genes express proteins, usually enzymes, that confer resistance to various antibiotics in cell culture. In other selective conditions, cells that express a fluorescent protein marker are made visible, and are thus selectable. Embodiments include beta-lactamase (bla) (beta-lactam antibiotic resistance or ampicillin resistance gene or ampR), bls (blasticidin resistance acetyl transferase gene), bsd (blasticidin-S deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene), and pac (puromycin resistance gene).

In certain embodiments, the vector comprises one or more selectable marker genes selected from the group consisting of bla, bls, BSD, bsr, Sh ble, hpt, tetR, tetM, npt, kanR and pac. In other embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), or yellow fluorescent protein (YFP).

For the purposes of this invention, gene expression in eukaryotic cells may be tightly regulated using a strong promoter that is controlled by an operator that is in turn regulated by a regulatory protein, which may be a recombinant "regulatory fusion protein" (RFP). The RFP consists essentially of a transcription blocking domain, and a ligand-binding domain that regulates its activity. Examples of such expression systems are described in US20090162901A1, which is herein incorporated by reference in its entirety.

As used herein "operator" indicates a DNA sequence that is introduced in or near a gene in such a way that the gene may be regulated by the binding of the RFP to the operator and, as a result, prevents or allow transcription of the gene of interest, i.e. a nucleotide encoding a polypeptide of the invention. A number of operators in prokaryotic cells and bacteriophage have been well characterized (Neidhardt, ed., *Escherichia coli* and *Salmonella*; Cellular and Molecular Biology 2d. Vol 2 ASM Press, Washington D.C. 1996). These include, but are not limited to, the operator region of the LexA gene of *E. coli*, which binds the LexA peptide, and the lactose and tryptophan operators, which bind the repressor proteins encoded by the LacI and trpR genes of *E. coli*. These also include the bacteriophage operators from the lambda PR and the phage P22 ant/mnt genes, which bind the repressor proteins encoded by lambda c1 and P22 arc. In some embodiments, when the transcription blocking domain of the RFP is a restriction enzyme, such as NotI, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

In an exemplary cell expression system, cells are engineered to express the tetracycline repressor protein (TetR) and a protein of interest is placed under transcriptional control of a promoter whose activity is regulated by TetR. Two tandem TetR operators (tetO) are placed immediately downstream of a CMV-MIE promoter/enhancer in the vector. Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription then translation (expression) of the protein of interest occurs. (See, e.g., U.S. Pat. No. 7,435,553, which is herein incorporated by reference in its entirety.)

The vectors of the invention may also employ Cre-lox recombination tools to facilitate the integration of a gene of interest into a host genome. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. (See, e.g. Araki et al., 1995, PNAS 92:160-4; Nagy, A. et al., 2000, Genesis 26:99-109; Araki et al., 2002, Nuc Acids Res 30(19):e103; and US20100291626A1, all of which are herein incorporated by reference). In another recombination strategy, yeast-derived FLP recombinase may be utilized with the consensus sequence FRT (see also, e.g. Dymecki, S. M., 1996, PNAS 93(12): 6191-6196).

As used herein, the term "host cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g. *S. cerevisiae, S. pombe, P. partoris, P. methanolica*, etc.), plant cells, insect cells (e.g. SF-9, SF-21, baculovirus-infected insect cells, *Trichoplusia ni*, etc.), non-human animal cells, mammalian cells, human cells, or cell fusions such as, for example, hybridomas or quadromas. In certain embodiments, the cell is a human, monkey, ape, hamster, rat or mouse cell. In other embodiments, the cell is eukaryotic and is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, W138, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g. a PER.C6@ cell). In some embodiments, the cell is a CHO cell. In other embodiments, the cell is a CHO K1 cell.

As used herein, the term "transformed cell of the invention" refers to a host cell comprising a nucleic acid stably integrated into the cellular genome that comprises a nucleotide sequence coding for expression of the peptide of the invention. In another embodiment, the present invention provides a cell comprising a non-integrated (i.e., episomal) nucleic acid, such as a plasmid, cosmid, phagemid, or linear expression element, which comprises a sequence coding for expression of a peptide of the invention. In other embodiments, the present invention provides a cell line produced by stably transfecting a host cell with a plasmid comprising an expression vector of the invention.

As used herein, the term "engineered" as applied to a cell means genetically engineered using recombinant DNA technology, and generally involves the step of synthesis of a suitable expression vector (see above) and then transfecting the expression vector into a host cell (generally stable transfection).

As used herein, the term "heterologous expression" refers to expression of a nucleic acid in a host cell that does not naturally have the nucleic acid. Insertion of the nucleic acid into the heterologous host is performed by recombinant DNA technology.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Hepatic Cell Penetration

Methodology

HepG2 (3×104 well-1) cells were seeded on 18 mm glass coverslips (Paul Marienfeld GmbH & Co. KG, Lauda-Königshofen, Germany) placed in a 24 well plate and adhered overnight in culture. Cells were treated with 0.5 µg/mL CY5 tagged pep_260 for 1h, after which they were fixed in 4% paraformaldehyde (Sigma, Arklow, Ireland) for 20 min at RT. Subsequently, the coverslips were washed in 1×PBS (Sigma, Arklow, Ireland) and incubated in 0.1% Tween 20 (Sigma, Arklow, Ireland) for 30 minutes at RT. The coverslips were then washed 3 times in 1×PBS for 5 min, and then treated with anti-human Early Endosome Antigen 1 (EEA1) rabbit monoclonal antibody (Cell Signalling Technology, Danvers, Massachusetts, USA) in a 1:500 dilution in PBS for overnight at 4 C. The coverslips were then washed 3 times in 1×PBS for 5 min. The 1×PBS was aspirated and the coverslips were treated with AlexaFluor 546 goat anti rabbit IgG (Life Technologies, Eugene, USA) in a 1:100 dilution in PBS for 2 hr at RT. The coverslips were then washed 3 times in 1×PBS for 5 min and treated with Hoechst 33342 solution (Thermo Scientific, Waltham, USA). The coverslips were then washed 3× times in PBS and removed with from the 24 well plates with a tweezers and mounted onto a Superfrost Plus microscope slide (Thermo Scientific, Waltham, USA) with 5 µL mowiol mounting medium [6 g glycerol (Sigma Aldrich), 2.4 g mowiol 4-88 (Sigma Aldrich) and 0.026 g 1,4-Diazabicyclo [2.2.2]octane (DABCO) (Sigma Aldrich) dissolved in 18 mL 0.2 M Tris-buffer (pH 8.5) (Sigma Aldrich).

Confocal images were captured with an Olympus Fluoview FV1000 Confocal Laser Scanning Biological Microscope (Shinjuku, Tokyo, Japan) with a 60×oil immersion objective. Hoechst nuclear staining was detected with a 405 nm Laser Diode, AlexaFlour 546 fluorophores were detected with a Diode-Pumped Solid-State laser and Cy5 tagged pep_260 was detected with a Solid-State Red Diode Laser.

Results

Confocal imaging demonstrates that pep_260 (SEQ ID 1) (red stain) is capable of penetrating HepG2 liver cells. This effect is observed after 5 mins of pep_260 treatment, with more profuse localisation within HepG2 cells seen at 60 mins (see FIG. 1).

In Vitro Study in Primary Human Primary Cell-Based Systems

Methodology

Human primary cells were used at early passage (passage 4 or earlier) to minimize adaptation to cell culture conditions and preserve physiological signaling responses. All cells are from a pool of multiple donors (n=2-6), commercially purchased and handled according to the recommendations of the manufacturers. Human blood derived CD14+ monocytes are differentiated into macrophages in vitro before being added to the IMphg system. Abbreviations are used as follows: Human umbilical vein endothelial cells (HUVEC), Peripheral blood mononuclear cells (PBMC), Human neonatal dermal fibroblasts (HDFn), B cell receptor (BCR), T cell receptor (TCR) and Toll-like receptor (TLR).

Cell types and stimuli used in each system are as follows: 3C system [HUVEC+(IL-13, TNFα and IFNγ)], 4H system [HUVEC+(IL-4 and histamine)], LPS system [PBMC and HUVEC+LPS (TLR4 ligand)], SAg system [PBMC and HUVEC+TCR ligands], BT system [CD19+ B cells and PBMC+(α-IgM and TCR ligands)], BF4T system [bronchial epithelial cells and HDFn+(TNFα and IL-4)], BE3C system [bronchial epithelial cells +(IL-1β, TNFα and IFNγ)], CASM3C system [coronary artery smooth muscle cells +(IL-1β, TNFα and IFNγ)], HDF3CGF system [HDFn+(IL-1β, TNFα, IFNγ, EGF, bFGF and PDGF-BB)], KF3CT system [keratinocytes and HDFn+(IL 1β, TNFα, IFNγ and TGFβ)], MyoF system [differentiated lung myofibroblasts+ (TNFα and TGFβ)] and IMphg system [HUVEC and M1 macrophages+Zymosan (TLR2 ligand)].

Systems are derived from either single cell types or co-culture systems. Adherent cell types are cultured in 96 or 384-well plates until confluence, followed by the addition of PBMC (SAg and LPS systems). The BT system consists of CD19+ B cells co-cultured with PBMC and stimulated with a BCR activator and low levels of TCR stimulation. Test agents prepared in either DMSO (small molecules; final concentration s 0.1%) or PBS (biologics) are added at the indicated concentrations 1-hr before stimulation, and remain in culture for 24 h or as otherwise indicated (48 h, MyoF system; 72 h, BT system (soluble readouts); 168 h, BT system (secreted IgG)). Each plate contains drug controls (e.g., legacy control test agent colchicine at 1.1 µM), negative controls (e.g., non-stimulated conditions) and vehicle controls (e.g., 0.1% DMSO) appropriate for each system. Direct ELISA is used to measure biomarker levels of cell-associated and cell membrane targets. Soluble factors from supernatants are quantified using either HTRF® detection, bead-based multiplex immunoassay or capture ELISA. Overt adverse effects of test agents on cell proliferation and viability (cytotoxicity) are detected by sulforhodamine B (SRB) staining, for adherent cells, and alamarBlue® reduction for cells in suspension. For proliferation assays, individual cell types are cultured at subconfluence and measured at time points optimized for each system (48 h: 3C and CASM3C systems; 72 h: BT and HDF3CGF systems; 96 h: SAg system). Cytotoxicity for adherent cells is measured by SRB (24 h: 3C, 4H, LPS, SAg, BF4T, BE3C, CASM3C, HDF3CGF, KF3CT, and IMphg systems; 48 h: MyoF system), and by alamarBlue staining for cells in suspension (24 h: SAg system; 42 h: BT system) at the time points indicated.

Results pep_260 (SEQ ID 1) mediated changes in key biomarker activities are listed by biological and disease classifications (see Table 1). pep_260 is not cytotoxic at the concentration tested in this study. pep_260 is antiproliferative to human primary endothelial cells.

TABLE 1

In vitro Primary Human Cell line biomarker profile in resposne to pep_260 treatment

| Biological/Disease Category | Biomarker | Activity |
| --- | --- | --- |
| Inflammation | VCAM-1, IL-8, IL-1a | ↓ |
| Immunomodulatory | sIL-2 | ↓ |
| Tissue remodelling | TIMP1 | ↓ |
| Hemostasis | TF | ↓ |
| Other activities | Anti proliferative: VEGFR2 | ↓ |

Hepatic Effects of Pep 260 (SEQ ID 1) in KKAy Mice

Methodology

The hepatic effects of pep_260 (SEQ ID 1) and liraglutide were evaluated in the KKAy obese diabetic mouse model. Male mice (n=11 per group), aged 12 weeks, were treated subcutaneously with pep_260 (12.7 & 63.5 mg/kg), liraglutide (250 µg/ml) or vehicle daily for 44 days. On day 44, animals were sacrificed by cervical dislocation 1 hour post treatment administration. For all animals, whole livers were collected and fixed in formalin. Liver tissue was sectioned and stained with hematoxylin and eosin. Histological steatosis was evaluated by an expert histopathologist blinded to the study groups according to the NALFD scoring system. Gene expression profiling in the liver was additionally performed.

Results

Expert grading demonstrates that treatment with pep_260 (SEQ ID 1) for 44 days significantly relieves macrovesicular steatosis in obese diabetic mice. Gene expression anaylses of liver tissue indicates that treatment with pep_260 (SEQ ID 1) induces a reduction in the SREBF1, FASN and Caspase-3 genes. These results indicate that pep_260 (SEQ ID 1) inhibits hepatic cholesterol production, inhibits hepatic lipogenesis and promotes hepatic cell survival.

Figure 2:
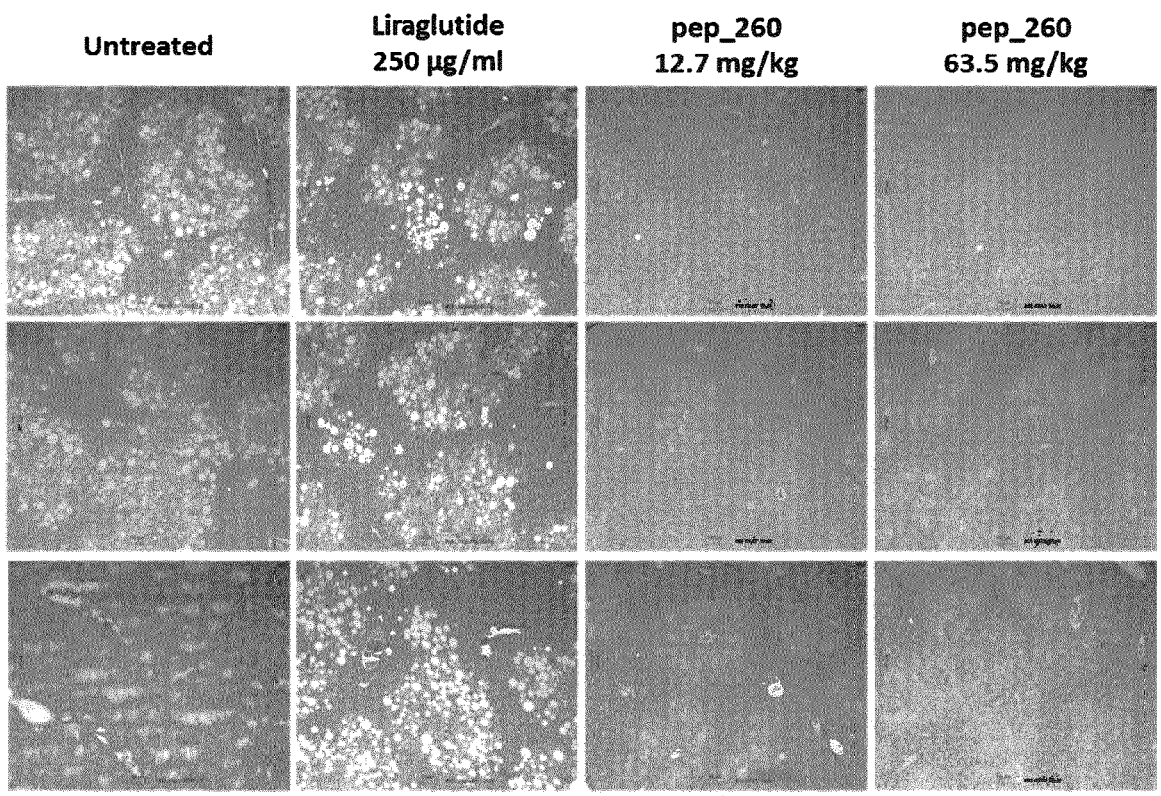
FIG. 2: Effect of pep_260 (SEQ ID 1) treatment on hepatic steatosis in KKAy mice. NALFD scoring was performed on liver tissue from each treatment group.
Figure 2:
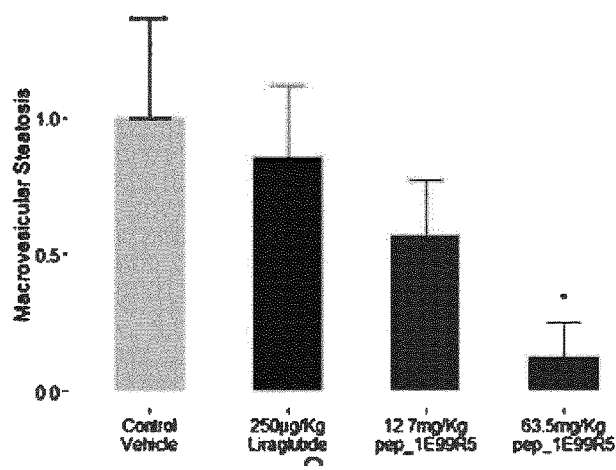
Figure 3:
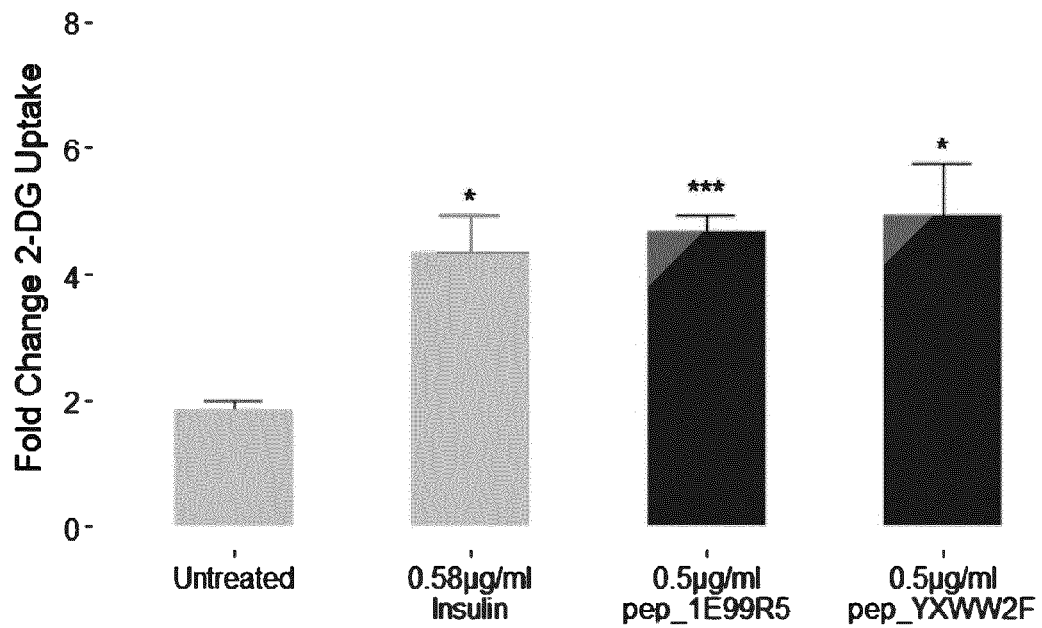
FIG. 3: Effect of variant peptide (pep_yxww2f=SEQ ID 2) on glucose update in skeletal muscle cells compared with insulin and peptide of the invention (pep_1E99R5=SEQ ID 1)

Vehicle control and Liraglutide-treated mice exhibited signs of NAFLD, however these were reduced significantly in 50 µM pep_1E99R5 and trended to a decrease in 10 µM pep_-1E99R5 treatment suggesting a dose-dependent effect (FIG. 2B).

IL-8 Secretion in Immortal Hepatocyte HepG2 Cells and Primary Lung Fibroblast WI-38 Cells Stimulated with LPS and TGFβ

Methodology

IL-8 Enzyme-Linked Immunosorbent Assay (ELISA):

HepG2 hepatocytes (density $1\times10^4$ cells/mL) were treated with 5 ng/ml of Pep_1E99R5, 10PANX (PANX1 mimetic) or PBS for 24 hours before LPS stimulation (100 ng/ml) to increase expression of IL-8 for a further 24 hours. Lipopolysaccharide (LPS) a known pro-inflammatory signal that increases the expression of IL-8 in vitro. IL-8 levels in culture supernatants were determined using a human IL-8-specific sandwich ELISA (Perkin Elmar, Waltham, Ma, USA) following the manufacturer's instructions.

Results

Figure 6:
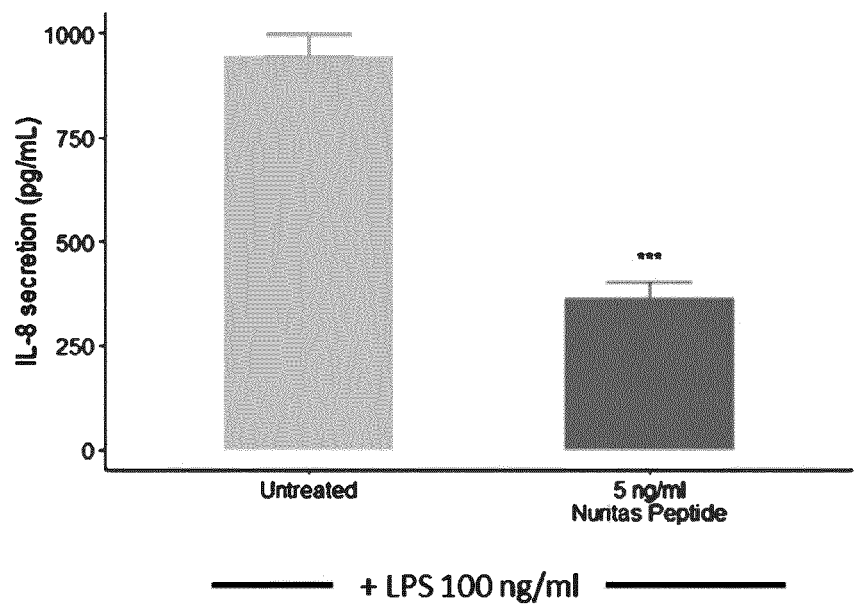
FIG. 6: Reduction in IL-8 secretion in HepG2 cells treated with pep_1E99R5 (pep_1 E99R5=SEQ ID 1) or 10PANX measured using sandwich ELISA. Cells were treated with either peptide (5 ng/ml), 10PANX (ug/mL) or PBS for 24 hrs before stimulation with 100 ng/ml LPS for a further 24 hours. Data presented as mean±SD of three independent experiments. ***$p≤0.001$ between replicates.

Results revealed that the expression of pro-inflammatory cytokine IL-8 was significantly reduced in cells pre-treated with pep_1E99R5 ($p<0.001$). This data provided further substantiation for beneficial effects regarding inflammation, for example, inflammatory aspects in NAFLD/NASH. Pro-inflammatory cytokine IL-8 which is strongly activated in NASH and contributes to hepatic inflammation and fibrosis (FIG. 6).

Anti-Fibrotic Effects of Pep 1E99R5 in TGF-β Stimulated Primary Hepatic Stellate Cells Initiation of Fibrosis in hepatic stellate cells (key inflammatory drivers of fibrosis induction in Liver Fibrosis and NASH/NAFLD) can be robustly modelled using incubation of primary human stellate cells with various concentrations of Transforming Growth Factor β (TGF-β).

Methodology

The procedure was performed as described above for the CY5 labelled peptide imaging in HSkMCs with a few minor modifications. Primary hepatic stellate cells were investigated as they are considered to be the most relevant profibrogenic cells operating in acute and chronic liver diseases. The stellate cells were seeded directly onto the glass coverslips at a density of 5,000 cells/mL. After starvation, the cells were treated with pep_1E99R5 (5 ng/mL) or Elafibranor (10 µM) for 6 hours. The cells were washed and subsequently treated with 5 ng/ml TGF-3 (Bio Techne, Minneapolis, MN, United States) for 24 hours to induce fibrosis. The cells were fixed and stained with ACTA2 antibody (Assay Genie, Dublin, Ireland), a marker of fibroblast activation.

The confocal images were analysed with custom Python scripts using the scikit-image library version 0.15. The cells and nuclei were segmented using a simple threshold computed using the mean value of the image. Using the Nuclei as a seed we separated the cells in the cell mask using watershed segmentation. Cell size was then quantified in pixels. [Stéfan van der Walt, Johannes L. Schönberger, Juan Nunez-Iglesias, Frangois Boulogne, Joshua D. Warner, Neil Yager, Emmanuelle Gouillart, Tony Yu and the scikit-image contributors. scikit-image: Image processing in Python. PeerJ 2:e453 (2014)

Results

Figure 4:
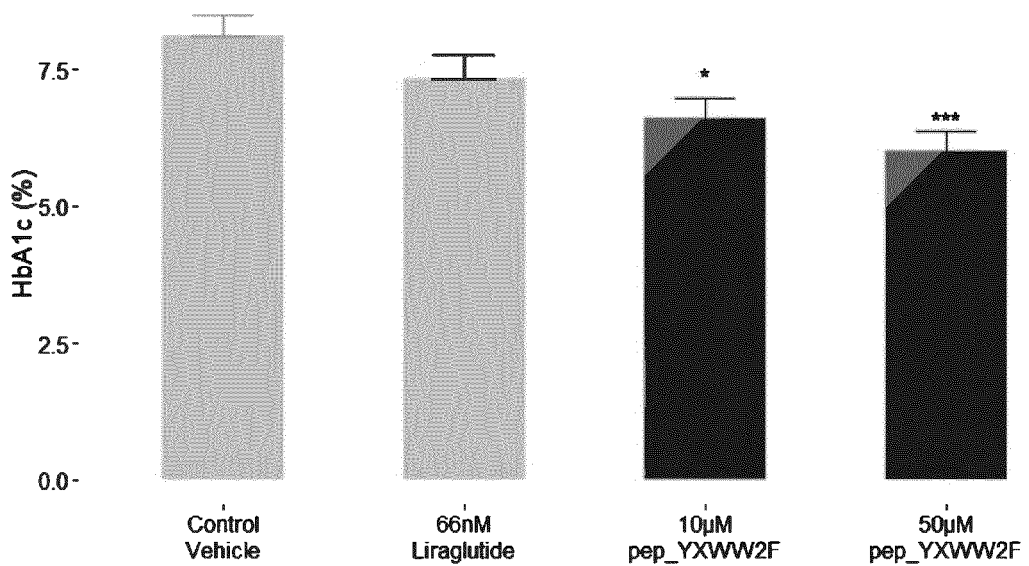
FIG. 4: (A) Effect of variant peptide (pep_yxww2f=SEQ ID 2) on glycosylated haemoglobin (HbA1c %) in skeletal muscle cells compared with Liraglutide. (B) Features were scored according to a murine liver scoring system devised by Sherwani S I, et al., Significance of HbA1c Test in Diagnosis and Prognosis of Diabetic Patients. *Biomark Insights*. 2016; 11:95-104. Data are mean±SEM (n=6 per group; aged 12 weeks at baseline) and analysed by Dunnett's test to compare the differences between the two peptide 50 treatment groups and vehicle control and Liraglutide groups (*$p<0.05$ $p<0.01$ *$p<0.001$)
Figure 5:
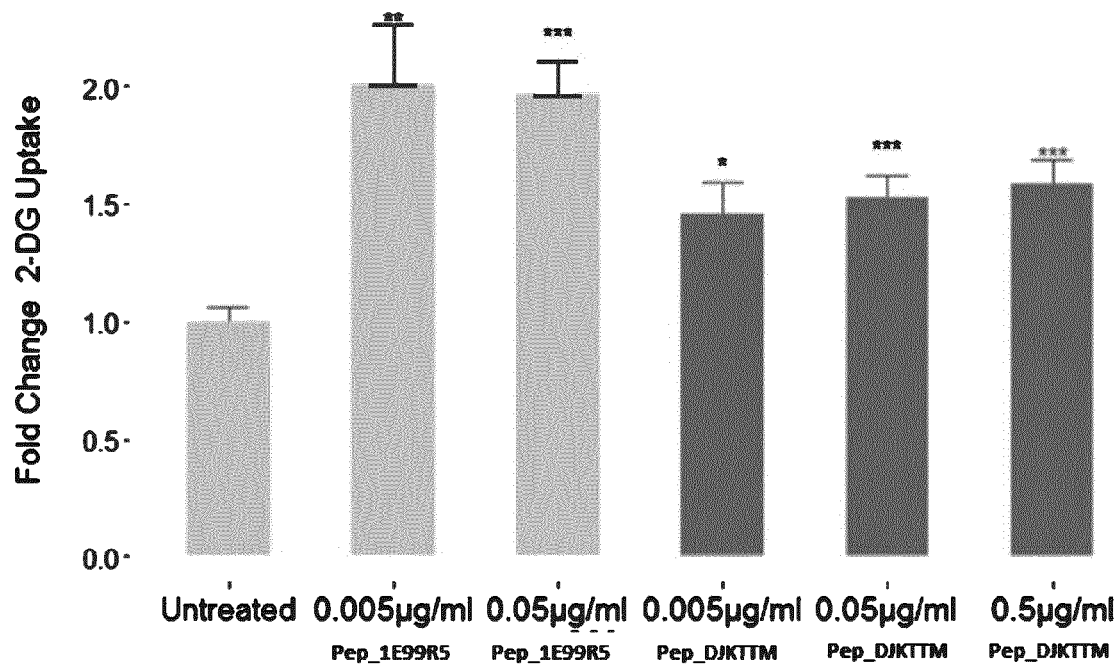
FIG. 5: Effect of variant cyclic peptide (pep_DJKTTM=SEQ ID 3) on glucose update in skeletal muscle cells compared with control and peptide of the invention (pep_1E99R5=SEQ ID 1).
Figure 7:
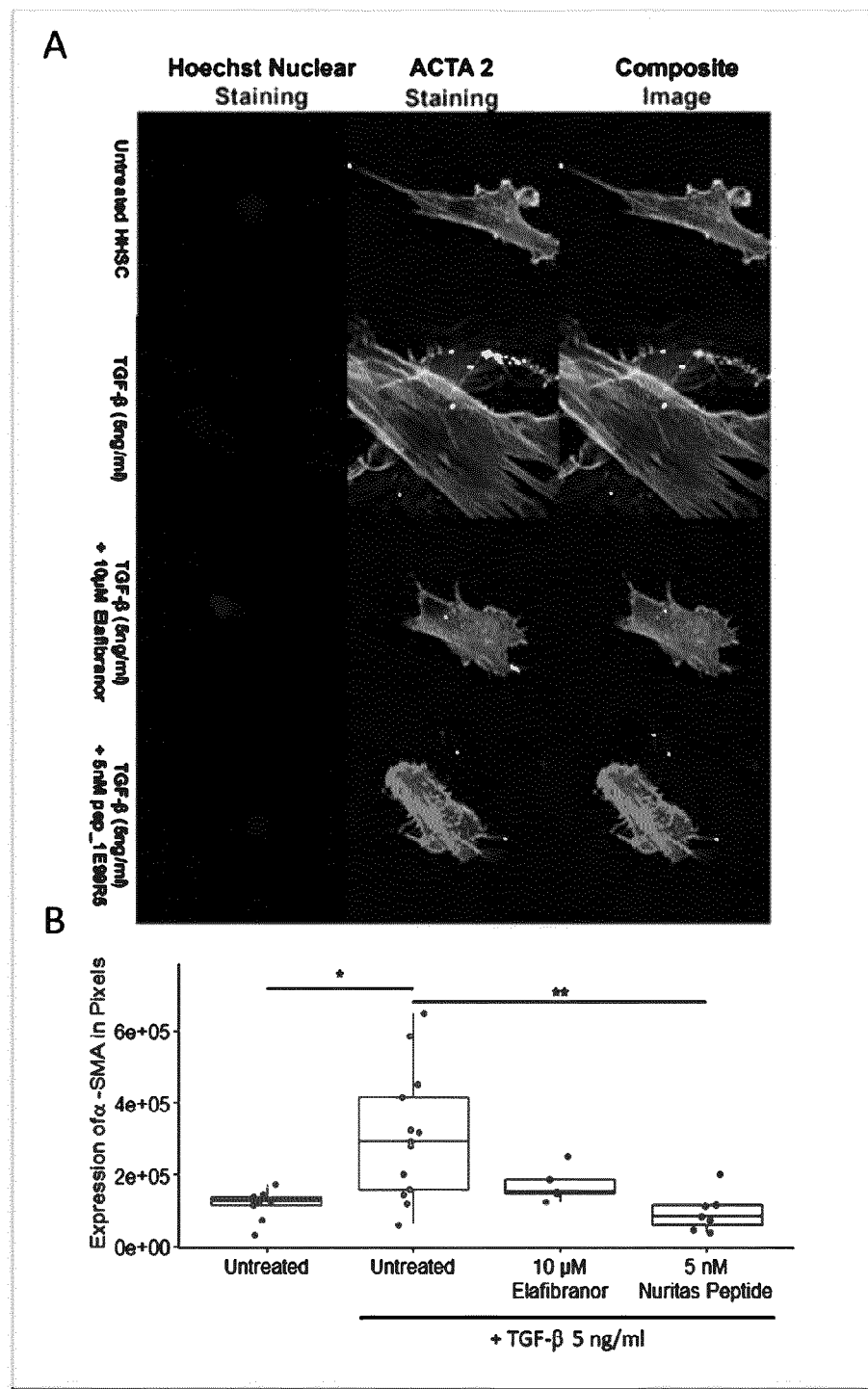
FIG. 7: pep_1E99R5 displays anti-fibrotic activity in stimulated primary human hepatic stellate cells. (A) Confocal imaging of human stellate cells treated with TGF-β to stimulate expression of α-SMA before treatment with Elafibranor (10 µM) or pep_1 E99R5 (5 nM). (B) Quantification of cell size in pixels for the treatment conditions, all conditions contain cells from 3 independent replciates. Untreated: x cells, Untreated+TGF betaxcells, Elafibranorx cells. (A). *$p<0.05$ between replicates, $p≤0.01$ between replicates, *$p≤0.001$ between replicates.

Stimulated primary hepatic stellate cells were used as a model of acute liver injury. Fluorescent images of untreated primary stellate cells, TGFβ stimulated cells (5 nM), Elafibranor treated (10 μM), and pep_1 E99R5 (5 nM) treated cells are shown in FIG. 4A. The TGF-3 stimulation was effective at inducing fibrosis in the cells (p<0.05). Increased ACTA2 expression, fibrogenesis, proliferation and morphological changes were observed in the stimulated cells which were absent in the control cells. Pre-incubation with pep_1E99R5 dramatically reduced the expression of the ACTA2 in the stellate cells, represented as the yellow fibres in the images (FIG. 7A). When the expression of the fibrosis marker was quantified in pixels using image analysis, this reduction was shown to be significant (p<0.01) and comparable with the anti-fibrotic effects of 10 μM Elafibranor (FIG. 7B).

Interestingly, the changes observed with pep_1E99R5 at 5 nM were comparable to those induced by Elafibranor (a lead clinical candidate with acting effects on stellate cells in vitro and in vivo) at 10 μM demonstrating a potentially better therapeutic profile for pep_1E99R5 as significantly lower concentrations were required to see the same effect.

This evidence coupled with unique protein target and biomarker fingerprint underlined the potential of this peptide entity to be deployed in a pre-clinical development programme against NASH/NAFLD.

APAP Model

Methodology

Animals for Acetaminophen (APAP)-induced Acute Liver Injury Mouse Model: All animal procedures were performed by Melior Discovery (Exton, PA, USA) in accordance with Institutional Animal Care and Use (IACUC) guidelines in an AAALAC-accredited facility. A pilot study was conducted prior to the APAP-induced hepatoxicity trail in order to establish an optimal APAP dose for the follow-up liver injury study (Supplemental FIG. 2). Studies were performed with 8-week-old male C57BL/6 mice obtained from the Charles River Laboratory and were randomly assigned to the treatment groups based on body mass. Mice were acclimated for 7 days and housed 4 per cage on a 12-hour light/dark cycle with ad libitum access to standard rodent chow and water. For the pilot study, mice were fasted overnight prior to intraperitoneal administration with a single dose of either APAP at 200 mpk, APAP at 300 mpk or saline as the control group. A total of 18 mice were included in the pilot study divided into 3 groups of 6 animals. Mice were subjected to tail bleeding for the first time point blood collection in order to reduce the stress and increase survival ability in mice. The blood samples from the 6-hour timepoint were used to yield serum samples for ALT and AST analysis. In the evaluation of the efficacy of the peptides in an APAP-induced acute liver injury mouse model APAP (200 mpk) was administered IP while both Pep_1E99R5 and 10PANX were administered intravenously at 10 mg/kg. 5 animals were included in each group with vehicle or peptides administered 1.5 hours post APAP injection. A survival bleed was performed at 2.25 and 6 hours for ALT/AST analysis. The terminal blood samples were collected via cardiac puncture, under isoflurane anaesthesia and used to yield serum samples for full-panel clinical chemistry analysis (data not shown).

Results

Figure 8:
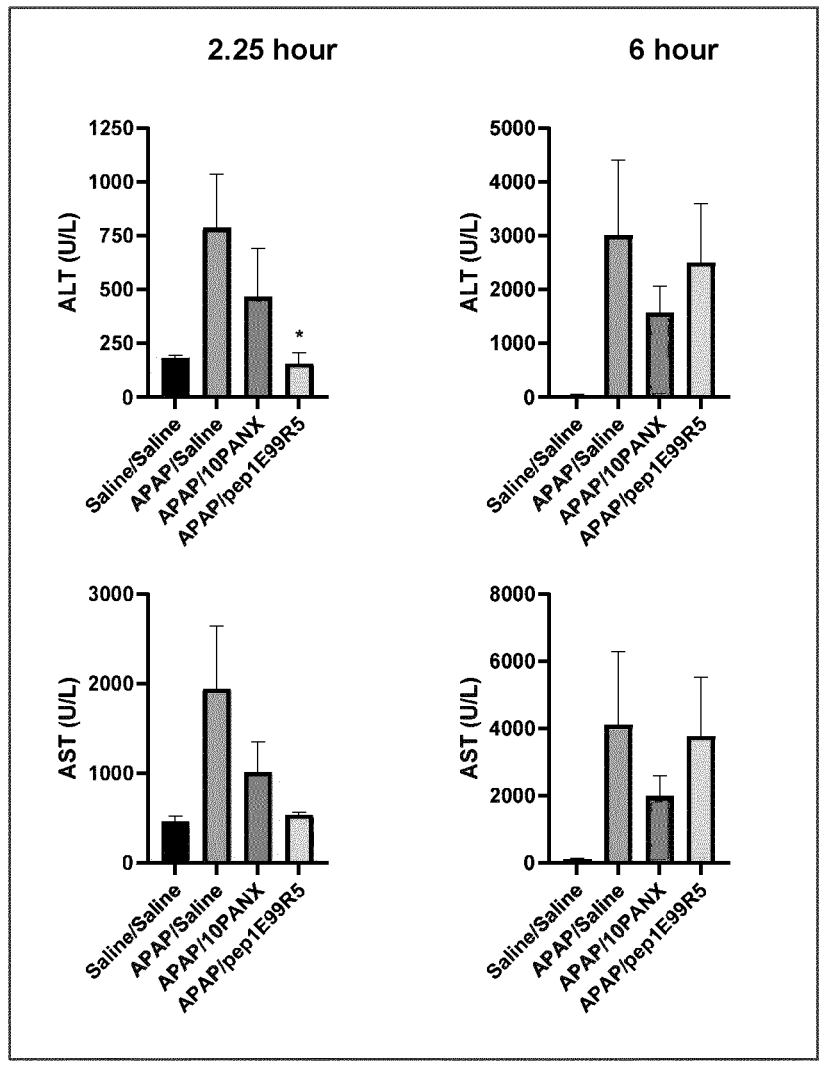
FIG. 8. Liver enzymes changes in the APAP acute liver injury mouse model study. APAP was administered via IP injection at 0 hours. Pep_1E99R5, 10PANX or saline control treatment was IV administered after 1.5 hours. 5 animals were included in each group. The levels of ALT and AST in all mice were measured from survival and terminal bleeds at 2.25 and 6 hours. At 2.25 hours, administration of pep_1E99R5 significantly reduced ALT levels ($p<0.05$) compared to the APAP/Saline treatment, and outperformed 10PANX. APAP/Saline group displayed increases in both ALT and AST, compared to Saline/Saline group. Data are mean±SEM and analysed by T-test followed by multiple comparisons tests as applicable.

The DiscoverX BioMap and Retrogenix screening results paired with the in vitro studies in both Hep-G2 and hepatic stellate cells strongly alluded towards the anti-inflammatory and anti-fibrotic effects of pep_1E99R5, therefore the either N-acetyl-para-aminophenol (APAP) model was conducted in order to assess the effects of the peptide in an in vivo liver injury model. The pilot study indicated that 200 mpk of APAP significantly increased the levels of both alanine aminotransferase (ALT) and aspartate aminotransferase (AST), biochemical hallmarks of APAP induced liver injury, in the mice versus the saline control. It was therefore considered as the optimum concentration for use in the liver injury trial. 1.5 hours after the initial APAP dosing, both peptides pep_1E99R5 and 10PANX were intravenously (IV) administered and the levels of the same liver enzymes were measured at 2.25 and 6 hours (FIG. 8). At the earlier timepoint, pep_1E99R5 significantly reduced the levels of ALT by 80% versus the APAP/saline control (p<0.05) and greatly outperformed 10PANX which induced a 41% reduction in ALT. A similar trend was observed in AST levels at 2.25 hours however significance was not achieved likely due to the small number of animals included in the study. By 6 hours the levels of ALT and AST in the APAP/saline group increased by 4 and 2-fold, respectively. The activity of 10PANX remained largely stable at this timepoint inducing a non-significant reduction in both liver enzymes between 45% and 52%. The levels of AST and ALT measured in the pep_1E99R5 treated mice increased at 6 hours in line with the APAP control animals. This gives an indication of the pharmacokinetic profile of pep_1E99R5 which appears to exhibit potent functionality for the first 2 hours and then likely becomes metabolised unlike 10PANX which persists for at least 3 times longer in the mice.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method for the treatment of non-alcoholic fatty liver disease (NAFLD) in a mammal having NAFLD, the method comprising:
administering:
(a) a peptide having up to 50 amino acids and comprising SEQ ID NO: 1, or
(b) a therapeutically effective variant of SEQ ID NO: 1 comprising 1 to 5 alterations compared with SEQ ID NO: 1, in which each alteration is independently selected from insertion of an amino acid, addition of an amino acid, deletion of an amino acid, and conservative substitution of an amino acid,
to the mammal.

2. The method of claim 1 wherein the non-alcoholic fatty liver disease is non-alcoholic steatohepatitis (NASH).

3. The method of claim 1 wherein the peptide consists of SEQ ID NO: 1.

4. The method of claim 1 wherein the method further comprises a step of administering a diabetes or obesity drug.

5. The method of claim 1, wherein one or more of the amino acids of SEQ ID NO: 1 are substituted with D-forms of the amino acids.

6. The method of claim 1 wherein at least two residues selected from residues 1, 2, 5, 10 and 11 of SEQ ID NO: 1 are substituted with a D-form of the amino acid.

7. The method of claim 1, wherein at least three or four residues selected from residues 1, 2, 5, 10 and 11 of SEQ ID NO: 1 are substituted with a D-form of the amino acid.

8. The method of claim 1, wherein the peptide comprises SEQ ID NO: 2.

9. The method of claim 1, wherein the peptide is cyclised.

10. The method of claim 1, wherein the peptide is a cyclised peptide of SEQ ID NO: 3.

* * * * *